United States Patent
Kraft

(10) Patent No.: US 7,687,452 B2
(45) Date of Patent: Mar. 30, 2010

(54) ORGANIC COMPOUNDS

(75) Inventor: Philip Kraft, Duebendorf (CH)

(73) Assignee: Givaudan SA, Vernier (CH)

( * ) Notice: Subject to any disclaimer, the term of this patent is extended or adjusted under 35 U.S.C. 154(b) by 696 days.

(21) Appl. No.: 11/568,475

(22) PCT Filed: May 4, 2005

(86) PCT No.: PCT/CH2005/000251

§ 371 (c)(1),
(2), (4) Date: Oct. 30, 2006

(87) PCT Pub. No.: WO2005/108534

PCT Pub. Date: Nov. 17, 2005

(65) Prior Publication Data

US 2007/0225201 A1    Sep. 27, 2007

(30) Foreign Application Priority Data

May 7, 2004    (GB)    ................... 0410134.1

(51) Int. Cl.
A61K 8/00     (2006.01)
A61K 8/18     (2006.01)
A61Q 13/00    (2006.01)
C07C 69/02    (2006.01)

(52) U.S. Cl. .............. 512/1; 512/22; 512/26; 560/231

(58) Field of Classification Search ............ 512/22, 512/1, 26; 560/259, 249, 231
See application file for complete search history.

(56) References Cited

U.S. PATENT DOCUMENTS 5,166,412 A     11/1992    Giersch et al.
6,384,269 B1 *   5/2002    Williams ................... 560/249

FOREIGN PATENT DOCUMENTS

| EP | 0 411 460 A | 2/1991 |
| EP | 1 182 190 A | 2/2002 |
| EP | 1262474 A | 12/2002 |
| JP | 7-310089 | 11/1995 |
| WO | 00/14051 A | 3/2000 |
| WO | 2004/050602 A | 6/2004 |

OTHER PUBLICATIONS

Fyna Foods Product Literature (http://www.fyna.com.au/downloads/Fyna_BLADS.pdf) 2004.*
CamiFlavors Product Literature (http://www.carmiflavors.com/) 1997-2004.*
International Search Report dated Aug. 10, 2005 for application PCT/CH2005/000251.
Written Opinion of the International Searching Authority for application PCT/CH2005/000251.
Search Report from The Patent Office in Great Britain dated Sep. 8, 2004 for application GB 0410134.1.
Patent Abstracts of Japan, vol. 1996, No. 3, Mar. 29, 1996 -& JP 07 310089 A (Ogawa Koryo KK), Nov. 28, 1995; abstract.

* cited by examiner

Primary Examiner—James Seidleck
Assistant Examiner—Aaron Greso
(74) Attorney, Agent, or Firm—Norris McLaughlin & Marcus, PA

(57) ABSTRACT

Alicyclic carboxylic acid oxycarbonylmethyl ester of formula (I)

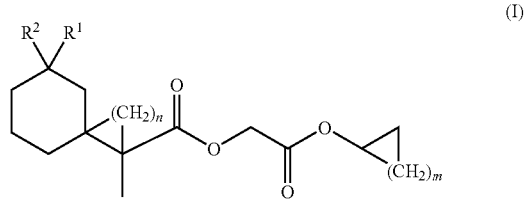

wherein $R^1$ and $R^2$ are independently hydrogen or $CH_3$, n is 0 or 1 and m is 0 or 1, and their use as odorants.

18 Claims, No Drawings

ORGANIC COMPOUNDS

This is an application filed under 35 USC 371 of PCT/CH2005/000251.

The present invention relates to novel alicyclic carboxylic acid oxycarbonylmethyl esters, and their use as odorants. This invention relates furthermore to a method of their production and to fragrance compositions comprising them.

In the fragrance industry there is a constant demand for new compounds that enhance or improve on odor notes, or impart new odor notes. It has now been found that certain alicyclic carboxylic acid oxycarbonylmethyl ester constitute new powerful musk odorants, particularly suitable for the use as fresh musky notes in fruity-green compositions, due to their unique fruity-musky character.

Accordingly, the present invention refers in one of its aspects to a compound of formula (I)

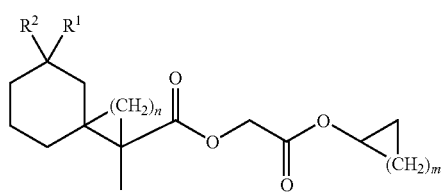

wherein $R^1$ and $R^2$ are independently hydrogen or $CH_3$;

n is 0 or 1; and m is 0 or 1.

The compounds according to the present invention contain several chiral centres, and as such may exist as a mixture of stereoisomers, or they may be resolved as isomerically pure forms. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methodology known in the art, e.g. preparative HPLC and GC or by stereoselective synthesis.

Particular preferred compounds of formula (I) are 2-(3,3-dimethylcyclohexyl)propionic acid ethoxycarbonylmethyl ester and 1,5,5-trimethylspiro[2.5]octane-1-carboxylic acid ethoxycarbonylmethyl ester.

The compounds according to the present invention may be used alone or in combination with known odorant molecules selected from the extensive range of natural and synthetic molecules currently available, such as ethereal oils and extracts, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

The following list comprises examples of known odorant molecules, which may be combined with the compounds of the present invention:

ethereal oils and extracts, e.g. castoreum, costus root oil, oak moss absolute, geranium oil, jasmine absolute, patchouli oil, rose oil, sandalwood oil or ylang-ylang oil.

alkohols, e.g. citronellol, Ebanol®, eugenol, geraniol, Super Muguet, linalool, phenylethyl alcohol, Sandalore®, terpineol or Timberol®.

aldehydes and ketones, e.g. Azurone™, α-amylcinnamaldehyde, Georgywood, hydroxycitronellal, Iso E Super, Isoraldeine, Hedione®, maltol, methyl cedryl ketone, methylionone or vanillin.

ethers and acetals, e.g. Ambrox®, geranyl methyl ether, rose oxide or Spirambrene®.

esters and lactones, e.g. benzyl acetate, cedryl acetate, γ-decalactone, Helvetolide®, γ-undecalactone or vetivenyl acetate.

macrocycles, e.g. ambrettolide, ethylene brassylate or Exaltolide®.

heterocycles, e.g. isobutylchinoline.

The compounds of the present invention may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other odorant ingredients. The proportion is typically from 0.001 to 20 weight percent of the application. In one embodiment, compounds of the present invention may be employed in a fabric softener in an amount of from 0.001 to 0.05 weight percent. In another embodiment, compounds of the present invention may be used in an alcoholic solution in amounts of from 0.1 to 30 weight percent, more preferably between 5 and 20 weight percent. However, these values are given only by way of example, since the experienced perfumer may also achieve effects or may create novel accords with lower or higher concentrations, e.g. up to about 50 weight percent based on the fragrance composition.

The compounds of the present invention may be employed into the fragrance application simply by directly mixing the fragrance composition with the fragrance application, or they may, in an earlier step be entrapped with an entrapment material such as for example polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application, comprising the incorporation therein of a compound of formula (I) as a fragrance ingredient, either by directly admixing the compound to the application or by admixing a fragrance composition comprising a compound of formula (I), which may then be mixed to a fragrance application, using conventional techniques and methods. Through the addition of an olfactory acceptable amount of a compound of the present invention, the odor notes of a fragrance application will be improved, enhanced or modified.

Thus, the invention furthermore provides a method for improving, enhancing or modifying a fragrance application through the addition thereto of an olfactory acceptable amount of a compound of formula (I).

As used herein, "fragrance application" means any products, such as fine fragrances, e.g. eaux de perfume and eaux de toilette; household products, e.g. detergents for dishwasher, surface cleaner; laundry products, e.g. softener, bleach, detergent; body care products, e.g. shampoo, shower gel; and cosmetics, e.g. deodorants, vanishing cremes, comprising an odorant. This list of products is given by way of illustration and is not to be regarded as being in any way limiting.

Compounds of formula (I) wherein n is 1, namely the optionally substituted spiro[2.5]octane-1-carboxylic acid oxycarbonylmethyl esters, may be prepared by Wittig-Horner-Emmons reaction of triethyl 2-phosphonopropionate with the corresponding cyclohexanone, followed by cyclopropanation of the formed α,β-unsaturated ester, saponification of the ester, and esterification of the resulting acid with the corresponding glycolate.

Compounds of formula (I) wherein n is 0, namely the optional substituted 2-(cyclohexyl)propionic acid esters, may be prepared by Wittig-Horner-Emmons reaction of triethyl 2-phosphonopropionate with the corresponding cyclohexanone, followed by saponification, esterification of the resulting acid with the corresponding glycolate and hydrogenation under standard conditions known to the person skilled in the art.

The invention is now further described with reference to the following non-limiting examples.

EXAMPLE 1

2-(3,3-Dimethylcyclohexyl)propionic acid ethoxycarbonylmethyl ester

A solution of triethyl 2-phosphonopropionate (79.8 g, 335 mmol) in 1,2-dimethoxy-ethane (70 ml) was added dropwise within 30 min to a stirred suspension of 95% NaH (7.54 g, 300 mmol) in 1,2-dimethoxyethane (350 ml). The reaction mixture was heated to reflux, and 3,3-dimethylcyclohexanone (63.0 g, 500 mmol) was added during a period of 5 min. After refluxing for 15 h, the reaction mixture was poured onto crushed ice (600 g), acidified to pH 5 by addition of AcOH (ca. 18 ml, 315 mmol), and extracted with $Et_2O$ (2×1 l). The combined organic extracts were washed with water and satd. aq. NaCl, dried ($MgSO_4$), and concentrated on the rotary evaporator to provide the crude α,β-unsaturated ester (89.2 g). Distillation in vacuo afforded at 89-90° C./3 mbar ethyl 2-(3,3-dimethylcyclohexylidene)propionate (61.3 g, 97%). The ethyl 2-(3,3-dimethyl-cyclohexylidene)propionate (30.0 g, 143 mmol) was dissolved in EtOH/water (1:1, 300 ml), and NaOH (28.6 g, 715 mmol) was added with stirring. After heating to reflux for 5 h, the EtOH was distilled off, and the reaction mixture was diluted with water (500 ml) prior to extraction. The ethereal washings were discarded, the aq. solution acidified with conc. $H_3PO_4$ and extracted with $Et_2O$ (3×700 ml). The combined organic extracts were dried ($MgSO_4$), and the solvent was evaporated on a rotary evaporator to furnish 2-(3,3-dimethylcyclohexylidene)propionic acid (24.6 g, 95%) sufficiently pure for further transformations. At 0° C., this crude 2-(3,3-dimethylcyclohexylidene)propionic acid (3.00 g, 16.5 mmol) was dissolved in $CH_2Cl_2$ (40 ml) and treated with ethyl glycolate (1.71 g, 16.4 mmol). Then, 4-dimethylaminopyridine (2.01 g, 16.5 mmol) was added at 0° C., and after stirring at this temperature for 5 min. a solution of 1,3-dicyclohexylcarbodiimide (3.74 g, 18.1 mmol) in $CH_2Cl_2$ (20 ml) was added dropwise. The cooling bath was removed, and stirring was continued at room temperature for 15 h before separating the precipitates by vacuum filtration. The precipitate was washed with $CH_2Cl_2$ (100 ml), and the combined filtrates were concentrated on the rotary evaporator. The crude product (7.55 g) was purified by silica-gel FC (pentane/$Et_2O$, 19:1) to provide 2-(3,3-dimethyl-cyclohexylidene)propionic acid ethoxycarbonylmethyl ester (3.96 g, 90%) as a colorless liquid of very weak odor. Pd 10% on activated carbon (0.10 g, 0.094 mmol) was added to a stirred solution of this 2-(3,3-dimethylcyclohexylidene)propionic acid ethoxycarbonylmethyl ester (1.00 g, 3.73 mmol) in EtOAc (10 ml). After two cycles of evacuating the reaction flask and flushing with $N_2$, the flask was evacuated again and flushed with $H_2$. After stirring in an $H_2$ atmosphere for 1 day, the reaction flask was again twice evacuated and flushed with $N_2$. The catalyst was separated by vacuum filtration over a pad of Celite® and washed with EtOAc (100 ml) to provide the crude material (1.02 g), which was purified by Kugelrohr-distillation to furnish at 75-85° C./0.04 mbar the odoriferous title compound 2-(3,3-dimethylcyclohexyl)propionic acid ethoxycarbonylmethyl ester (0.96 g, 96%).

IR (neat): ν=1744 s, 1764 m (ν C=OO); 1144 s (ν C—O). $^1$H-NMR ($CDCl_3$): 0.90 (s, $Me_2C(3')$); 0.91-1.60 (m, $CH_2$ (2'), $CH_2(4')$, $CH_2(5')$, $CH_2(6')$); 1.15/1.16 (d, J=7.5, $CH_3(3)$); 1.28 (t, J=7.0, $CH_3(5''')$); 1.76 ($m_c$, H—C(1')); 2.29/2.30 (quint, J=7.5, H—C(2)); 4.22 (q, J=7.0, $CH_2(4''')$); 4.60 (s, $CH_2(1''')$). $^{13}$C-NMR ($CDCl_3$): 13.7/13.8/13.9/14.0 (q, C(5''', 3)); 22.0/22.1 (t, C(5')); 24.4/24.5 (q, $Me_{ax}$-C(3')); 29.0/30.8 (t, C(6')); 30.6/30.7 (s, C(3')); 33.3/33.4 (q, $Me_{eq}$-C(3')); 36.1/36.2 (d, C(1')); 38.8/38.9 (t, C(4')); 42.4/43.9 (t, C(2')); 45.1/45.2 (d, C(2)); 60.3/60.3/61.0/61.1 (t, C(1''', 4''')); 167.7/167.8 (s, C(2''')); 175.6/175.7 (s, C(1)). MS (70 eV): 270 (1, $M^+$), 255 (1, $[M-Me]^+$), 225 (8, $[M-EtO]^+$), 185 (5, $C_{11}H_{21}O_2^+$), 167 (11, $[C_{11}H_{21}O_2—H_2O]^+$), 160 (100, $C_7H_{12}O_4^+$, McLafferty rearr.), 114 (78, $[C_7H_{12}O_4-EtOH]^+$), 95 (54, $C_7H_{11}^+$), 69 (48, $C_5H_9^+$), 56 (59, $C_4H_8^+$).

Odor description: Musky, fruity, rhubarb, slightly rosy.

EXAMPLE 2

1,5,5-Trimethylspiro[2.5]octane-1-carboxylic acid ethoxycarbonylmethyl ester In $N_2$ atmosphere, AgOAc (120 mg, 0.719 mmol) was dissolved in AcOH (125 ml). At reflux, Zn powder (20.2 g, 309 mmol) was added with stirring, and after additional 10 min. stirring at reflux temperature the heating source was removed. The supernatant was decanted, and the residue washed with AcOH (100 ml) and $Et_2O$ (5×100 ml). The insoluble material was then suspended in $Et_2O$ (250 ml), and a catalytic amount of Ag wool was added under $N_2$. To this suspension was added at room temperature with vigorous stirring ethyl 2-(3,3-dimethylcyclohexylidene)propionate (25.0 g, 119 mmol), prepared according to Example 1. Subsequently, $CH_2I_2$ (41.4 g, 155 mmol) was added dropwise with stirring within 10 min at this temperature, and then the reaction mixture was refluxed for 24 h, before addition of further $CH_2I_2$ (20.7 g, 77.3 mmol). After another 64 h stirring at reflux temperature, the heating bath was removed; the reaction mixture was allowed to cool to room temperature, and poured into saturated aq. $NH_4Cl$. The organic layer was separated, and the aqueous one extracted twice with $Et_2O$. The combined organic extracts were washed with water, 40% aq. $NaHSO_4$ and brine, dried ($MgSO_4$) and concentrated on the rotary evaporator to give the crude material (26.5 g). This was then dissolved in hexane (200 ml) and $Br_2$ (1.55 ml) was added dropwise with stirring at room temperature within 30 min. After stirring for 2 h at room temperature, the mixture was poured onto crushed ice (500 g). The organic layer was separated, and the aqueous one extracted twice with $Et_2O$. The combined organic extracts were washed with saturated aq. $NaHCO_3$, water and brine. After drying ($MgSO_4$) and evaporation of the solvent on the rotary evaporator, the resulting residue was purified by FC on silica gel (pentane/$Et_2O$, 99:1, $R_f$=0.55) to provide 1,5,5-trimethylspiro[2.5]octane-1-carboxylic acid ethyl ester (22.3 g, 84%). This 1,5,5-trimethylspiro[2.5]octane-1-carboxylic acid ethyl ester (17.0 g, 75.8 mmol) was dissolved in EtOH/water (1:1, 300 ml), and NaOH (15.2 g, 380 mmol) was added with stirring. After heating to reflux for 5 h, the EtOH was distilled off, and the reaction mixture was diluted with water (500 ml) prior to extraction.

The ethereal washings were discarded, the aq. solution acidified with conc. $H_3PO_4$ and extracted with $Et_2O$ (3×700 ml). The combined organic extracts were dried ($MgSO_4$), and the solvent was evaporated on a rotary evaporator to furnish 1,5,5-trimethylspiro[2.5]octane-1-carboxylic acid (13.9 g, 94%) sufficiently pure for further transformations. At 0° C., this crude 1,5,5-trimethylspiro[2.5]octane-1-carboxylic acid (1.50 g, 7.64 mmol) was dissolved in $CH_2Cl_2$ (20 ml) and treated with ethyl glycolate (790 mg, 7.59 mmol). Then, 4-dimethylaminopyridine (0.18 g, 1.48 mmol) was added at 0° C., and after stirring at this temperature for 5 min. a solution of 1,3-dicyclohexylcarbodiimide (1.73 g, 8.38 mmol) in $CH_2Cl_2$ (20 ml) was added dropwise. The cooling bath was removed, and stirring was continued at room temperature for 15 h before separating the precipitates by vacuum filtration. The precipitate was washed with $CH_2Cl_2$ (50 ml), and the combined filtrates were concentrated on the rotary evaporator. The crude product (3.77 g) was purified by silica-gel FC (pentane/$Et_2O$, 19:1, $R_f$=0.48) to provide 1,5,5-trimethylspiro[2.5]octane-1-carboxylic acid ethoxycarbonylmethyl ester (1.76 g, 82%) as an odoriferous liquid.

IR (neat): ν=1131 s (ν C—O); 1731 s, 1764 m (ν C=OO). $^1$H-NMR ($CDCl_3$): 0.52/0.53 (d, J=24.5, $CH_2$(2)); 0.83/0.93 (s, Me-C(1)); 0.94 (s, $Me_2$-C(5)); 1.11-1.62 (m, $CH_2$(4), $CH_2$(6), $CH_2$(7), $CH_2$(8)); 1.29 (t, J=7.0, $CH_3$(5')); 4.21/4.22 (q, J=7.0, $CH_2$(4')); 4.60 (s, $CH_2$(1')). $^{13}$C-NMR ($CDCl_3$): 13.9/14.0 (q, C(5')); 15.6/16.1 (q, Me-C(1)); 21.3/21.4 (t, C(7)); 25.9/26.6 (t, C(8)); 26.9/27.1 (q, $Me_{ax}$-C(5)); 27.2/27.6 (s, C(5)); 30.3/33.4 (q, $Me_{eq}$-C(5)); 30.5/31.5 (t, C(2)); 29.5/30.0131.7/31.8 (s, C(1,3)); 39.0/39.1 (t, C(6)); 42.0/43.4 (t, C(4)); 60.7/60.8/61.0/61.1 (t, C(1', 4')); 167.9/168.0 (s, C(2')); 173.7/173.8 (s, 1-C=O). MS (70 eV): 282 (1, $M^+$), 237 (3, $[M-EtO]^+$), 178 (43, $[M-C_4H_8O_3]^+$), 163 (24, $[M-C_4H_8O_3-Me]^+$), 150 (8, $C_{11}H_{18}^+$), 135 (21, $[M-C_4H_8O_3—C_3H_7]^+$), 122 (25, $C_8H_{10}O^+$), 109 (100, $C_8H_{13}^+$), 95 (26, $C_7H_{11}^+$), 81 (16, $[C_8H_{13}^+—C_2H_4]^+$), 69 (56, $C_5H_9^+$), 41 (42, $C_3H_5^+$).

Odor description: Musky, fruity.

EXAMPLE 3 to 12

Following the general procedure of example 1 and 2, the compounds 3 to 12 of Table 1 may be prepared accordingly.

TABLE 1

|    | $R^1$ | $R^2$ | n | m | Name |
|----|-------|-------|---|---|------|
| 3  | $CH_3$ | $CH_3$ | 0 | 1 | 2-(3,3-Dimethylcyclohexyl)propionic acid cyclopropoxycarbonylmethyl ester |
| 4  | $CH_3$ | H | 0 | 0 | 2-(3-Methylcyclohexyl)propionic acid ethoxycarbonylmethyl ester |
| 5  | $CH_3$ | H | 0 | 1 | 2-(3-Methylcyclohexyl)propionic acid cyclopropoxycarbonylmethyl ester |
| 6  | H | H | 0 | 0 | 2-Cyclohexyl-propionic acid ethoxycarbonylmethyl ester |
| 7  | H | H | 0 | 1 | 2-Cyclohexylpropionic acid cyclopropoxycarbonylmethyl ester |
| 8  | $CH_3$ | $CH_3$ | 1 | 1 | 1,5,5-Trimethylspiro[2.5]octane-1-carboxylic acid cyclopropoxycarbonylmethyl ester |
| 9  | $CH_3$ | H | 1 | 0 | 1,5-Dimethylspiro[2.5]octane-1-carboxylic acid ethoxycarbonylmethyl ester |
| 10 | $CH_3$ | H | 1 | 1 | 1,5-Dimethylspiro[2.5]octane-1-carboxylic acid cyclopropoxycarbonylmethyl ester |
| 11 | H | H | 1 | 0 | 1-Methylspiro[2.5]octane-1-carboxylic acid ethoxycarbonylmethyl ester |
| 12 | H | H | 1 | 1 | 1-Methylspiro[2.5]octane-1-carboxylic acid cyclopropoxycarbonylmethyl ester |

EXAMPLE 13

Fruity-Green Accord for Female Perfumes

| Ingredient | Parts per weight |
|---|---|
| 1. Bergamot oil | 40 |
| 2. para-tert-Butylcyclohexyl acetate | 150 |
| 3. Citral | 5 |
| 4. para-Cresyl methyl ether | 5 |
| 5. gamma-Decalactone | 4 |
| 6. 4,5-Dimethyl-3-hydroxy-2[5H]-furanone @ 1% in triethyl citrate (TEC) | 2 |
| 7. Dodecanal | 2 |
| 8. Guaiyl acetate | 10 |
| 9. (3Z)-Hex-3-enol @ 10% in dipropylene glycol (DPG) | 4 |
| 10. Hexyl acetate | 50 |
| 11. beta-Ionone | 40 |
| 12. Linalool | 20 |
| 13. Linalyl acetate | 13 |
| 14. Methyl dihydrojasmonate | 100 |
| 15. 3-Methyl-5-(2,2,3-trimethyl-3-cyclopenten-1-yl)-4-penten-2-ol | 1 |
| 16. Nonayl acetate | 50 |
| 17. Octahydrocoumarin | 10 |
| 18. Phenoxyethyl alcohol | 140 |
| 19. 2-Phenylethyl acetate | 12 |
| 20. 2-Phenylethyl alcohol | 80 |
| 21. Sweet Orange Oil | 50 |
| 22. 3a,6,6,9a-Tetramethyldodecahydronaphto[2,1-b]furan | 2 |
| 23. (6E)-3,7,11-Trimethyl-6,10-dodecadienal | 30 |
| 24. 1,7,7-Trimethyl-2'-(isopropyl)-spiro-(bicyclo[2.2.1]heptane-2,4'-[1,3]dioxane) @ 50% in isopropyl myristate | 30 |
| 25. 2-(3,3-Dimethylcyclohexyl)propionic acid ethoxycarbonylmethyl ester | 150 |
| Total: | 1000 |

2-(3,3-Dimethylcyclohexyl)propionic acid ethoxycarbonylmethyl ester brings radiance and freshness to this fragrance. It lifts the lactonic top note and provides a sensual musky touch in the dry-down. Altogether, it adds elegance, crispness and volume to the fragrance. Besides the main musk note, the fruity, rhubarb-like facettes of the 2-(3,3-dimethylcyclohexyl)propionic acid ethoxycarbonylmethyl ester harmonize very well with the fruity accord; thus, leading to a unique blend, in which also the floral side of the 2-(3,3-dimethylcyclohexyl)propionic acid ethoxycarbonylmethyl ester comes into play.

The invention claimed is:
1. A compound of formula (I)

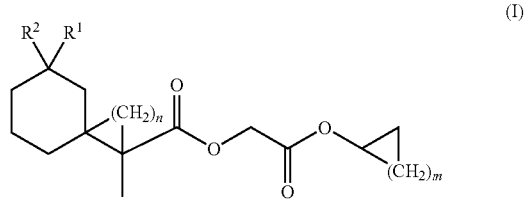

wherein $R^1$ and $R^2$ are independently hydrogen or $CH_3$; n is 0 or 1; and m is 0 or 1.

2. A compound according to claim 1 selected from the group consisting of:
- 2-(3,3-dimethylcyclohexyl)propionic acid ethoxycarbonylmethyl ester,
- 1,5,5-trimethylspiro[2.5]octane-1-carboxylic acid ethoxycarbonylmethyl ester,
- 2-(3,3-dimethylcyclohexyl)propionic acid cyclopropoxycarbonylmethyl ester,
- 2-(3-methylcyclohexyl)propionic acid ethoxycarbonylmethyl ester,
- 2-(3-methylcyclohexyl)propionic acid cyclopropoxycarbonylmethyl ester,
- 2-cyclohexyl-propionic acid ethoxycarbonylmethyl ester,
- 2-cyclohexylpropionic acid cyclopropoxycarbonylmethyl ester,
- 1,5,5-trimethylspiro[2.5]octane-1-carboxylic acid cyclopropoxycarbonylmethyl ester,
- 1,5-dimethylspiro[2.5]octane-1-carboxylic acid ethoxycarbonylmethyl ester,
- 1,5-dimethylspiro[2.5]octane-1-carboxylic acid cyclopropoxycarbonylmethyl ester,
- 1-methylspiro[2.5]octane-1-carboxylic acid ethoxycarbonylmethyl ester and
- 1-methylspiro[2.5]octane-1-carboxylic acid cyclopropoxycarbonylmethyl ester.

3. An odorant compound according to formula (I) according to claim 1.

4. A flavour composition comprising a compound of formula (I) according to claim 1.

5. A method of manufacturing a flavour composition, comprising the step of: incorporating a compound of formula (I) according to claim 1 into a base material.

6. A method of manufacturing a fragrance application, comprising the incorporation of a compound of formula (I) according to claim 1 into said fragrance application.

7. A method for improving, enhancing or modifying a fragrance application through the addition of an olfactory acceptable amount of a compound of formula (I) according to claim 1 into said fragrance application.

8. A method according to claim 6 wherein the fragrance application is selected from the group consisting of perfumes, household products, laundry products, body care products and cosmetics.

9. An odorant compound according to claim 2.

10. A flavour composition comprising a compound according to claim 2.

11. A method of manufacturing a flavour composition, comprising the step of: incorporating a compound according to claim 2 into a base material.

12. A method of manufacturing a fragrance application, comprising the incorporation of a compound according to claim 2 into said fragrance application.

13. A method for improving, enhancing or modifying a fragrance application through the addition of an olfactory acceptable amount of a compound according to claim 2 into said fragrance application.

14. A method according to claim 7 wherein the fragrance application is selected from the group consisting of perfumes, household products, laundry products, body care products and cosmetics.

15. A fragrance composition comprising a compound of formula (I) according to claim 1.

16. A method of manufacturing a fragrance composition, comprising the step of: incorporating a compound of formula (I) according to claim 1 into a base material.

17. A fragrance composition comprising a compound according to claim 2.

18. A method of manufacturing a fragrance composition, comprising the step of: incorporating a compound according to claim 2 into a base material.

* * * * *